United States Patent
Lee et al.

(10) Patent No.: US 7,758,810 B2
(45) Date of Patent: Jul. 20, 2010

(54) CENTRIFUGAL FORCE BASED MICROFLUIDIC DEVICE, MICROFLUIDIC SYSTEM INCLUDING THE SAME, AND METHOD OF DETERMINING HOME POSITION OF THE MICROFLUIDIC DEVICE

(75) Inventors: Jeong-gun Lee, Seoul (KR); Beom-seok Lee, Yongin-si (KR); Jong-myeon Park, Seoul (KR); Jung-suk Yoo, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 442 days.

(21) Appl. No.: 11/875,973

(22) Filed: Oct. 22, 2007

(65) Prior Publication Data
US 2008/0252905 A1  Oct. 16, 2008

(30) Foreign Application Priority Data
Apr. 16, 2007  (KR) .................... 10-2007-0037164

(51) Int. Cl.
*G01N 21/07* (2006.01)
*G01B 11/00* (2006.01)
(52) U.S. Cl. .................. 422/72; 422/82.05; 356/614
(58) Field of Classification Search .................. 422/72, 422/82.05; 356/614
See application file for complete search history.

(56) References Cited

U.S. PATENT DOCUMENTS

| 6,338,820 | B1 | 1/2002 | Hubbard et al. |
| 6,992,278 | B2 | 1/2006 | Sjoberg et al. |
| 2002/0085202 | A1 | 7/2002 | Gordon |
| 2003/0094502 | A1 | 5/2003 | Anderson et al. |

FOREIGN PATENT DOCUMENTS

GB         2293876 A         4/1996

OTHER PUBLICATIONS

C.A. Burtis, et al., Development of a Multi-Purpose Optical System for Use with a Centrifugal Fast Analyzer, 1975, Clinical Chemistry, 21 (9): 1225-1233.*

* cited by examiner

*Primary Examiner*—Jill Warden
*Assistant Examiner*—Timothy G Kingan
(74) *Attorney, Agent, or Firm*—Sughrue Mion, PLLC

(57) ABSTRACT

Provided is a centrifugal force based microfluidic system including: a microfluidic device including a rotatable platform and an optical path formed to extend horizontally in a straight line from a circumference of the platform; a motor rotating so as to control the microfluidic device; a light emitting unit emitting light towards the microfluidic device; a light receiving unit detecting the light emitted from the light emitting unit; and a controller determining a home position to be the position of the microfluidic device at a point of time when the light emitted from the light emitting unit is detected by the light receiving unit, wherein the light emitted from the light emitting unit passes through the optical path to be incident on the light receiving unit only when the microfluidic device is located in a predetermined position.

19 Claims, 5 Drawing Sheets

CENTRIFUGAL FORCE BASED MICROFLUIDIC DEVICE, MICROFLUIDIC SYSTEM INCLUDING THE SAME, AND METHOD OF DETERMINING HOME POSITION OF THE MICROFLUIDIC DEVICE

CROSS-REFERENCE TO RELATED PATENT APPLICATION

This application claims priority from Korean Patent Application No. 10-2007-0037164, filed on Apr. 16, 2007, in the Korean Intellectual Property Office, the disclosure of which is incorporated herein in its entirety by reference.

BACKGROUND OF THE INVENTION

1. Field of the Invention

Apparatuses consistent with the present invention relate to a centrifugal force based microfluidic device, a microfluidic system including the microfluidic device and a method of determining a home position of the microfluidic device using the microfluidic system.

2. Description of the Related Art

Generally, a microfluidic device has a structure which includes a chamber storing a minute amount of a fluid, a channel through which the fluid flows, a valve for controlling flow of the fluid, and various functional units receiving the fluid to perform predetermined functions thereon. A biochip is obtained by arranging such a microfluidic device on a chip-type substrate and is used to analyze the performance of various assays including biologic reactions. In particular, a device that is designed to perform multiple step processes and manipulations using a single chip is referred to as a lab-on-a-chip.

A driving pressure is generally required to transfer a fluid within a microfluidic device. Capillary pressure or pressure generated by a specifically prepared pump is used to create the driving pressure. A lab compact disk (CD) or a lab-on a disk is a recently-suggested microfluidic device obtained by arranging microfluidic structures on a compact disk-shaped platform and uses centrifugal forces. This is referred to as a lab CD or a lab-on-a-disk.

Such centrifugal force based microfluidic devices perform sample reactions according to their own uses (e.g. immune serum tests and gene test) in chambers. Reaction results are detected through corresponding reaction detectors. In order to perform the sample reactions in the microfluidic devices and detect the reaction results using the reaction detectors, it is necessary that positions of valves, functional units, and chambers for detecting the reaction disposed on a disk-type platform should be correctly determined.

FIG. 1 is a plan view of a related art microfluidic device, which is disclosed in U.S. Pat. No. 6,992,278.

Referring to FIG. 1, a mark 15 is made on a circumference of a platform 11 of the related art microfluidic device 10 to mark a home position. By emitting light onto the mark 15 to detect reflected light and setting the mark 15 as the home position, relative positions of valves, functional units and chambers can be determined. However, in the related art, the mark 15 should be formed to have a relatively large size in order to reduce detection errors for the home position. In addition, since light may be diffused, determination error for the home position may be increased during emitting and reflecting light.

SUMMARY OF THE INVENTION

The present invention provides a centrifugal force based microfluidic device that is improved to increase the precision of the determining of a home position, a microfluidic system including the microfluidic device and a method of determining a home position of the microfluidic device using the microfluidic system.

According to an aspect of the present invention, there is provided a centrifugal force based microfluidic device including: a rotatable platform; and an optical path formed to extend horizontally in a straight line from a circumference side of the platform.

According to another aspect of the present invention, there is provided a centrifugal force based microfluidic system including: a microfluidic device comprising a rotatable platform and an optical path formed to extend horizontally in a straight line from a circumference side of the platform; a motor rotating so as to control the microfluidic device; a light emitting unit emitting light towards the microfluidic device; a light receiving unit detecting the light emitted from the light emitting unit; and a controller determining a home position to be the position of the microfluidic device at the time when the light emitted from the light emitting unit is detected by the light receiving unit, wherein the light emitted from the light emitting unit passes through the optical path to be incident on the light receiving unit only when the microfluidic device is located in a predetermined position.

The optical path may be a hole or a groove formed on the platform.

The groove may be formed from an upper or lower surface of the platform.

The optical path may be formed to cross the platform from one side of the circumference of the platform to another side of the circumference of the platform, and the platform may be disposed between the light emitting unit and the light receiving unit so that the light emitted from the light emitting unit passes through the optical path to be incident on the light receiving unit.

A motor mounting hole, in which the motor is mounted, may be formed in the center of the platform, the optical path is formed to extend in a straight line through the motor mounting hole, and a through hole may be s formed in the motor so that the optical path is not blocked.

A motor mounting hole, in which the motor is mounted, may be formed in the center of the platform, the optical path is formed to extend from one side of the circumference of the platform to the motor mounting hole, the motor may include a reflective surface reflecting light that is emitted by the light emitting unit to be incident on the motor along the optical path, and the light receiving unit may be disposed on the one same side, on which the light emitting unit is formed, so as to detect the light reflected by the reflective surface.

The system may further include a half mirror passing the light emitted by the light emitting unit and reflecting the light reflected by the reflective surface of the motor towards the light receiving unit.

The light receiving unit may include a light emitting diode (LED) or a laser diode (LD).

The light receiving unit may include a photo diode.

According to another aspect of the present invention, there is provided a method of determining a home position of a microfluidic device including: rotating the microfluidic device including a rotatable platform and an optical path formed to extend horizontally in a straight line from the circumference of the platform; emitting light towards the microfluidic device by using a light emitting unit; and determining the home position to be the position of the microfluidic device at the point of time when the emitted light passes through the optical path to be detected in a light receiving unit.

The optical path may be formed to cross the platform from one side of the circumference of the platform to another side of the circumference of the platform, and the light emitted from the light emitting unit in the emitting of light may pass through the optical path in the determining of the home position to be incident on the light receiving unit facing the light emitting unit, wherein the platform may be disposed between the light emitting unit and the light receiving unit.

A motor mounting hole, in which a motor comprising a through hole formed therein is mounted to rotate so as to control the microfluidic device, may be formed in the center of the platform, the optical path is formed to extend in a straight line through the motor mounting hole, and the light emitted from the light emitting unit in the emitting of the light may be incident on the light receiving unit through the through hole in the determining of the home position.

A motor mounting hole, in which a motor comprising a reflective surface is mounted to rotate so as to control the microfluidic device, may be formed in the center of the platform, the optical path may be formed to extend from one side of the circumference of the platform to the motor mounting hole, and the light emitted from the light emitting unit in the emitting of the light may be reflected by the reflective surface of the motor along the optical path in the determining of the position to be incident on the light receiving unit disposed on the same side on which the light emitting unit is formed.

The light reflected by the reflective surface of the motor in the determining of the position may be further reflected by a half mirror to be emitted towards the light receiving unit.

BRIEF DESCRIPTION OF THE DRAWINGS

The above and other aspects of the present invention will become more apparent by describing in detail exemplary embodiments thereof with reference to the attached drawings, in which.

DETAILED DESCRIPTION OF EXEMPLARY EMBODIMENTS

The present invention will now be described more fully with reference to the accompanying drawings, in which exemplary embodiments of the invention are shown. The invention may, however, be embodied in many different forms and should not be construed as being limited to the embodiments set forth herein; rather, these exemplary embodiments are provided so that this disclosure will be thorough and complete, and will fully convey the concept of the invention to those skilled in the art.

Figure 1:
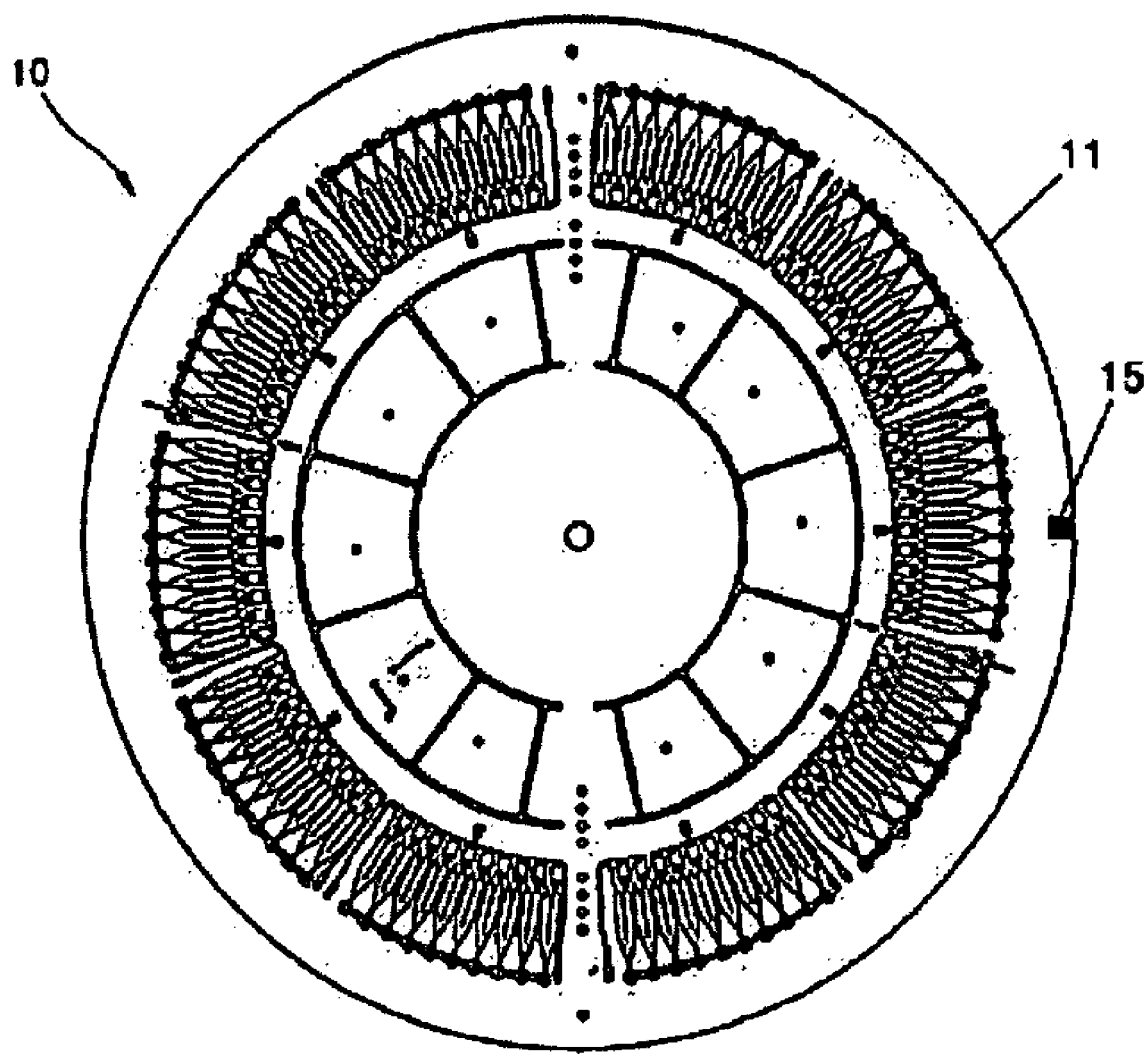
FIG. 1 is a plan view of a related art microfluidic device.
Figure 2:
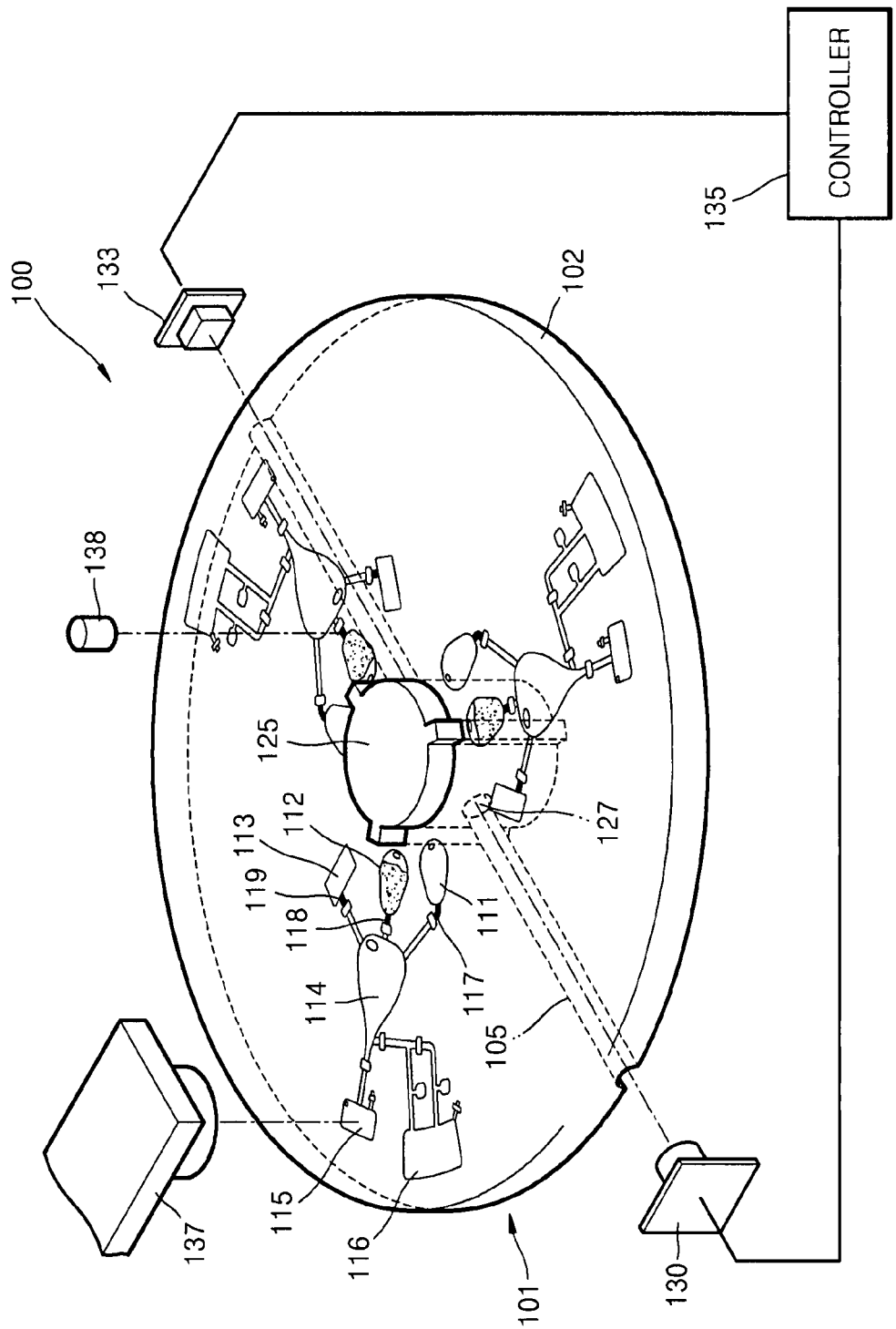
FIG. 2 is a perspective view of a microfluidic system according to an exemplary embodiment of the present invention.
Figure 3:
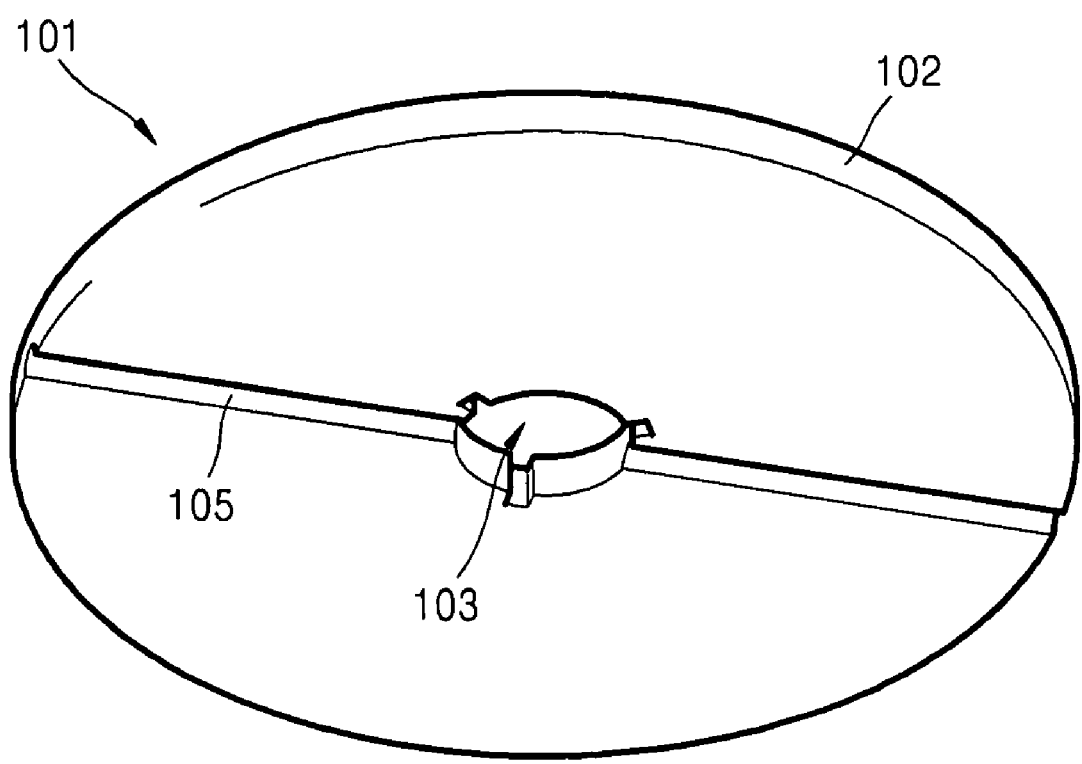
FIG. 3 is a perspective view of a microfluidic device illustrated in FIG. 2, which is viewed from below, according to an exemplary embodiment of the present invention.

FIG. 2 is a perspective view of a microfluidic system 100 according to an exemplary embodiment of the present invention. FIG. 3 is a perspective view of a microfluidic device 101 illustrated in FIG. 2, which is viewed from below.

Referring to FIGS. 2 and 3, the microfluidic system 100 includes a microfluidic device 101 including a rotatable disk-type platform 102, a spindle motor 125 that is a kind of motor rotating so as to control the microfluidic device 101, and a light emitting unit 130, a light receiving unit 133 and a controller 135 for determining a home position of the microfluidic device 101.

The microfluidic device 101 includes a chamber keeping a small quantity of a predetermined fluid on the platform 102, a channel along which a fluid flows, a valve regulating the flow of a fluid or various functional units receiving a fluid to perform predetermined functions. Specifically, the microfluidic device 101 illustrated in FIG. 2 is a microfluidic device designed to perform an immunoassay and detect a result thereof, and includes a sample chamber 111, a bead chamber 112, a mix chamber 114, a buffer chamber 113, a waist chamber 116 and a reaction chamber 115.

The sample chamber 111 is a place housing a sample such as a serum. The bead chamber 112 is a place housing beads mixed with the sample. The mix chamber 114 is a place to house a predetermined detection probe combined with the beads after capturing predetermined protein. In the mix chamber 114, the sample, the beads and the detection probe are mixed. The buffer chamber 113 is a place housing a buffer that dilutes and rinses a mixing solution of the sample, the beads and the detection probe, and discharges residue. The waist chamber 116 is a place housing the discharged residue. The reaction chamber 115 is a place housing predetermined substrate and enzyme reacting with the detection probe that is attached to the beads and moved together with the beads. The detection probe and the substrate react with each other to realize an optical signal. The microfluidic system 100 further includes a reaction detector 137 for detecting the optical signal due to the reaction.

The sample chamber 111, the bead chamber 112 and the buffer chamber 113 are connected to the mix chamber 114. Valves 117, 118 and 119 controlling the flow of the fluid are arranged in each of channels. The valves 117, 118 and 119 usually close the channel, but open the channels under a predetermined condition. These valves may be called normally closed valves. The microfluidic system 100 further includes an external energy source 138 for providing energy to the valves 117, 118 and 119. The external energy source 138 may be a laser light source emitting a laser beam.

The microfluidic device 101 includes an optical path 105 extending horizontally along in a straight line from a circumference side of the platform 102 through the center of the microfluidic device 101 and to the other side of the microfluidic device 101. The optical path 105 is a groove formed on a lower surface of the platform 102. Although the optical path 105 is illustrated to be a curved groove in FIGS. 2 and 3, the present invention is not limited thereto. That is, an optical path may be a hole. In addition, an optical path may be a groove formed not on a lower surface of a platform but on an upper surface of the platform. The optical path 105 is formed to cross the platform 102 from one side of the platform 102 to other side of the platform 102. A spindle motor mounting hole 103, in which a spindle motor 125 is mounted, is disposed in the center of the optical path 105. A through hole 127 is formed in the spindle motor 125 so that the optical path 105 extending in an imaginary straight line may not be blocked by the spindle motor 125 mounted in the spindle motor mounting hole 103.

The light emitting unit 130 emits light in a horizontal direction towards the rotating microfluidic device 101, and may include a light emitting diode (LED) emitting a visible ray or a laser diode (LD) emitting a laser beam. When the microfluidic device 101 is located in a predetermined position during its rotating, an emission direction of light emitted from the light emitting unit 130 coincides with an extending direction of the optical path 105 included in the platform 102. Accordingly, only at this time, the light emitted from the light emitting unit 130 can pass through the platform 102 along the optical path 105, and the position of the microfluidic device 101 at this time can be determined as the home position. The longer the optical path 105 is and the narrower the groove is, the higher the precision of determining the home position is.

The light receiving unit 133 detects the light that is emitted from the light emitting unit 130 to pass through the platform 102, and may include a photodiode detecting incident light using photovoltaic effect. The light receiving unit 133 faces the light emitting unit 130, wherein the platform 102 is disposed between the light receiving unit 133 and the light emitting unit 130. The controller 135 may be a computer (not shown) connected to communicate with the light emitting unit 130, the light receiving unit 133, the reaction detector 137 and the external energy source 138. The controller 135 determines the home position to be the position of the microfluidic device 101 at the time when the light emitted from the light emitting unit 130 is detected as being incident on the light receiving unit 133.

Hereinafter, a method of determining the home position of the microfluidic device 101 using the microfluidic system 100 will now be described. First, the microfluidic device 101 is equipped with the spindle motor 125. The spindle motor 125 is driven to be rotated. At this time, the through hole 127 of the spindle motor 125 and the optical path 105 are aligned so that the optical path 105 of the microfluidic device 101 may not be blocked by the spindle motor 125. Next, light is emitted towards the rotating microfluidic device 101 using the light emitting unit 130. When the emitted light passes through the optical path 105 to be incident on the light receiving unit 133, the position of the microfluidic device 101 at this time is determined to be the home position.

Since the controller 135 stores information on a relative position of the reaction chamber 115, in which reaction needs to be detected, and information on relative positions of the valves 117, 118 and 119, to which energy needs to be provided, in the microfluidic device 101, the controller 135 determines the home position as described above to appropriately control the spindle motor 125 to rotate the microfluidic device 101 by an angle corresponding to the relative position of the reaction chamber 115 or the relative positions of the valves 117, 118 and 119, and thus the reaction chamber 115 can be aligned below the reaction detector 137, or one of the valves 117, 118 and 119 can be aligned below the external energy source 138.

Figure 4:
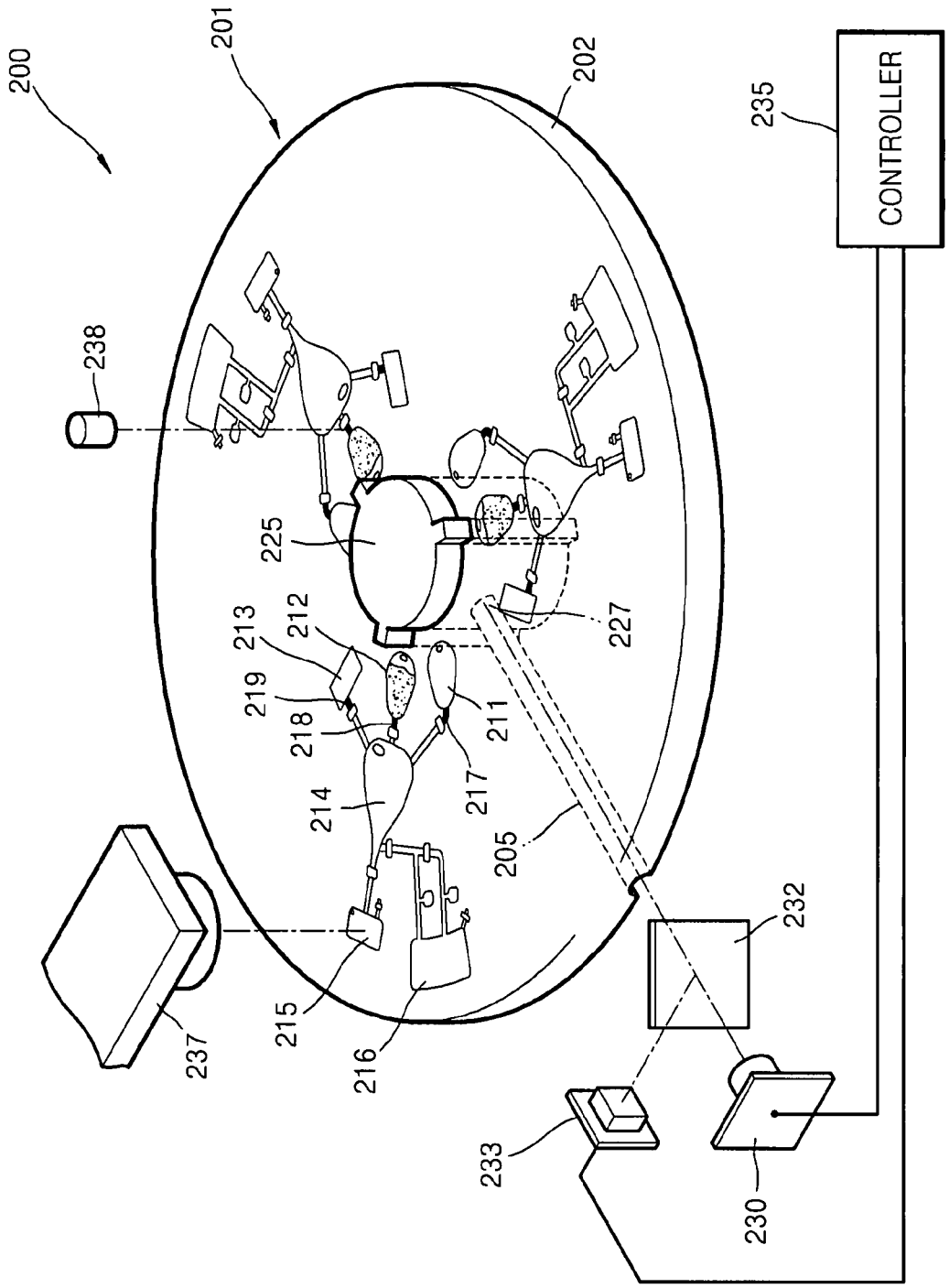
FIG. 4 is a perspective view of a microfluidic system according to another exemplary embodiment of the present invention.
Figure 5:
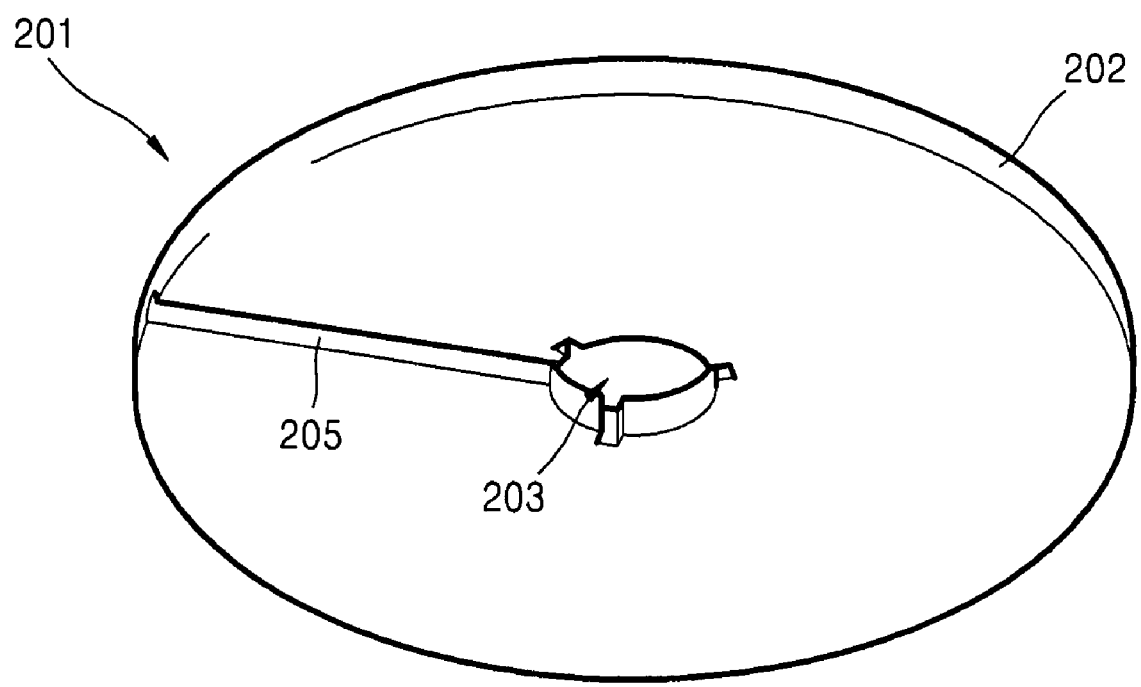
FIG. 5 is a perspective view of a microfluidic device illustrated in FIG. 4, which is viewed from below, according to an exemplary embodiment of the present invention.

FIG. 4 is a perspective view of a microfluidic system 200 according to another exemplary embodiment of the present invention. FIG. 5 is a perspective view of a microfluidic device 201 illustrated in FIG. 4, which is viewed from below.

Referring to FIGS. 4 and 5, the microfluidic system 200 includes a microfluidic device 201 including a disk-type platform 202, a spindle motor 225 rotating the microfluidic device 201, and a light emitting unit 230, a light receiving unit 233 and a controller 235 for determining a home position of the microfluidic device 101.

The microfluidic device 201 includes a chamber keeping a small quantity of a predetermined fluid on the platform 202, a channel along which a fluid flows, a valve regulating the flow of a fluid or various functional units receiving a fluid to perform predetermined functions. That is, the microfluidic device 201 illustrated in FIG. 4 is a microfluidic device designed to perform an immunoassay and detect a result thereof, similarly to the microfluidic device 100 illustrated in FIG. 2, and includes a sample chamber 211, a bead chamber 212, a mix chamber 214, a buffer chamber 213, a waist chamber 216, a reaction chamber 215 and valves 217, 218 and 219 controlling the flow of a fluid. Since the functions of the chambers 211, 212, 213, 214, 215 and 216 and the valves 217, 218 and 219 are same as those of the chambers 111, 112, 113, 114, 115 and 116 and the valves 117, 118 and 119 that are illustrated in FIG. 2, their repeated descriptions will be omitted. The microfluidic system 200 further includes a reaction detector 237 detecting an optical signal due to the immunoassay and an external energy source 238 providing energy to the valves 217, 218 and 219. The external energy source 238 may be a laser light source irradiating a laser beam.

The microfluidic device 201 includes an optical path 205 extending horizontally in a straight line from a circumference side of the platform 202. The optical path 205 is a groove formed on a lower surface of the platform 202. Although the optical path 205 is illustrated to be a groove in FIGS. 4 and 5, the present invention is not limited thereto. That is, the optical path may be a hole.

A spindle motor mounting hole 203, in which a spindle motor 225 is mounted, is disposed in the center of the platform 202. The optical path 205 is formed to extend from one circumference side of the platform 202 to the spindle motor mounting hole 203. The spindle motor 225 mounted in the spindle motor mounting hole 203 includes a reflective surface 227 reflecting light incident on the spindle motor 225 along the optical path 205. The reflective surface 227 may be formed using a method in which all of or a part of the circumference side of the spindle motor 225 is coated with a metal capable of reflecting light.

The light emitting unit 230 emits light in a horizontal direction towards the rotating microfluidic device 201, and may include an LED emitting a visible ray or a laser diode (LD) emitting a laser beam. When the microfluidic device 201 is located in a predetermined position during its rotating, an emission direction of light emitted from the light emitting unit 230 coincides with an extending direction of the optical path 205 included in the platform 202. Accordingly, only at this time, the light emitted from the light emitting unit 230 can be incident on the reflective surface 227 of the spindle motor 225 along the optical path 205, and can be reflected by the reflective surface 227. The position of the microfluidic device 201 at this time can be determined as the home position. The longer the optical path 205 is and the narrower the groove is, the higher the precision of determining the home position is.

The light receiving unit 233 detects the light that is reflected on the reflective surface 227 and proceeds toward the circumference side of the platform 202 along the optical path 205. The light receiving unit 233 is disposed on the same side on which the light emitting unit 230 is located. The light receiving unit 233 may include a photodiode detecting incident light using photovoltaic effect.

The microfluidic system 200 includes a half mirror 232 disposed between the light emitting unit 230 and the platform 202. The half mirror 232 passes light emitted towards the microfluidic device 201 from the light emitting unit 230, and reflects light, which is reflected on the reflective surface 227 and proceeds toward the circumference side of the platform 202, toward the light receiving unit 233.

The controller 235 may be a computer (not shown) connected to communicate with the light emitting unit 230, the light receiving unit 233, the reaction detector 237 and the external energy source 238. The controller 235 determines the home position to be the position of the microfluidic device 201 at the time when the light emitted from the light emitting unit 230 is detected as being incident on the light receiving unit 233.

Hereinafter, a method of determining the home position of the microfluidic device 201 using the microfluidic system 200 will now be described. First, the microfluidic device 201 is equipped with the spindle motor 225. The spindle motor 225 is driven to be rotated. At this time, the microfluidic device 201 is aligned so that the reflective surface 227 of the spindle motor 225 may face an end of the spindle motor mounting hole 203 of the optical path 205. Next, light is emitted towards the rotating microfluidic device 201 using the light emitting unit 230. When the emitted light passes through the half mirror 232 to be reflected by the reflective surface 227, and is again reflected by the half mirror 232 to be detected, the position of the microfluidic device 201 is determined as the home position.

Since the controller 235 stores information on a relative position of the reaction chamber 215, in which a reaction is to be detected, and information on relative positions of the valves 217, 218 and 219, to which energy needs to be provided, in the fluidic device 201, the controller 235 determines the home position as described above to appropriately control the spindle motor 225 to rotate the microfluidic device 201 by an angle corresponding to the relative position of the reaction chamber 215 or the relative positions of the valves 217, 218 and 219, and thus the reaction chamber 215 can be aligned below the reaction detector 237, or the valves 217, 218 and 219 can be aligned below the external energy source 238.

According to the present invention, the precision of determining the home position can be increased with respect to the related art. The precision of determining the home position can be further increased as the optical path is longer and narrower.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A centrifugal force based microfluidic device comprising:
    a rotatable platform; and
    an optical path formed to extend horizontally in a straight line from a circumference of the platform,
    wherein the optical path is formed to cross the platform from one point of the circumference of the platform to another point of the circumference of the platform.

2. The device of claim 1, wherein the optical path is a hole or a groove formed in the platform.

3. The device of claim 2, wherein the groove is formed on an upper or lower surface of the platform.

4. The device of claim 1, wherein a motor mounting hole, in which a motor that rotates so as to control the microfluidic device is mounted, is formed in a center of the platform, and the optical path is formed to extend in a straight line through the motor mounting hole.

5. The device of claim 1, wherein a motor mounting hole, in which a motor rotates the microfluidic device to control the microfluidic device, is formed in a center of the platform, and
    wherein the optical path is formed to extend from one point of the circumference of the platform to the motor mounting hole.

6. A centrifugal force based microfluidic system comprising:
    a microfluidic device comprising a rotatable platform and an optical path formed to extend horizontally in a straight line from a circumference of the platform;
    a motor that rotates so as to control the microfluidic device;
    a light emitting unit that emits light toward the microfluidic device;
    a light receiving unit that detects the light emitted from the light emitting unit; and
    a controller that determines a home position to be a position of the microfluidic device at a time when the light emitted from the light emitting unit is detected by the light receiving unit,
    wherein the light emitted from the light emitting unit passes through the optical path to be incident on the light receiving unit only when the microfluidic device is located in a predetermined position, and
    wherein the optical path is formed to cross the platform from one point of the circumference of the platform to another point of the circumference of the platform.

7. The system of claim 6, wherein the optical path is a hole or a groove formed in the platform.

8. The system of claim 7, wherein the groove is formed on an upper or lower surface of the platform.

9. The system of claim 6, wherein the optical path is formed to cross the platform from one point of the circumference of the platform to another point of the circumference of the platform, and
    wherein the platform is disposed between the light emitting unit and the light receiving unit so that the light emitted from the light emitting unit passes through the optical path to be incident on the light receiving unit.

10. The system of claim 9, wherein a motor mounting hole, in which the motor is mounted, is formed in a center of the platform,
    wherein the optical path is formed to extend in a straight line through the motor mounting hole, and
    wherein a through hole is formed in the motor so that the optical path is not blocked.

11. The system of claim 6, wherein a motor mounting hole, in which the motor is mounted, is formed in a center of the platform,
    wherein the optical path is formed to extend from one point of the circumference of the platform to the motor mounting hole,
    wherein the motor comprises a reflective surface reflecting the light that is emitted by the light emitting unit to be incident on the motor along the optical path, and
    wherein the light receiving unit is disposed on a same side, on which the light emitting unit is located, so as to detect the light reflected by the reflective surface.

12. The system of claim 11, further comprising a half mirror that passes the light emitted by the light emitting unit and reflects the light reflected by the reflective surface of the motor toward the light receiving unit.

13. The system of claim 6, wherein the light receiving unit comprises a light emitting diode (LED) or a laser diode (LD).

14. The system of claim 6, wherein the light receiving unit comprises a photo diode.

15. A method of determining a home position of a microfluidic device, the method comprising:
- rotating the microfluidic device comprising a rotatable platform and an optical path formed to extend horizontally in a straight line from one point of the circumference of the platform to another point of the circumference of the platform;
- emitting light toward the microfluidic device by using a light emitting unit; and
- determining the home position to be a position of the microfluidic device at a time when the emitted light passes through the optical path to be detected by a light receiving unit.

16. The method of claim 15, wherein the optical path is formed to cross the platform from one point of the circumference of the platform to another point of the circumference of the platform,
- wherein the light emitted from the light emitting unit passes through the optical path to be incident on the light receiving unit facing the light emitting unit, and
- wherein the platform is disposed between the light emitting unit and the light receiving unit.

17. The method of claim 16, wherein a motor mounting hole, in which a motor comprising a through hole formed therein is mounted to rotate so as to control the microfluidic device, is formed in a center of the platform,
- wherein the optical path is formed to extend in a straight line through the motor mounting hole, and
- wherein the light emitted from the light emitting unit is incident on the light receiving unit through the through hole.

18. The method of claim 15, wherein a motor mounting hole, in which a motor comprising a reflective surface is mounted to rotate so as to control the microfluidic device, is formed in a center of the platform,
- wherein the optical path is formed to extend from one point of the circumference of the platform to the motor mounting hole, and
- wherein the light emitted from the light emitting unit is reflected by the reflective surface of the motor along the optical path to be incident on the light receiving unit disposed on a same side on which the light emitting unit is formed.

19. The method of claim 18, wherein the light reflected by the reflective surface of the motor is further reflected by a half mirror to be emitted toward the light receiving unit.

* * * * *